United States Patent
Hase

[11] Patent Number: 6,030,844
[45] Date of Patent: Feb. 29, 2000

[54] METHOD AND APPARATUS FOR PRE-ANALYZING TREATMENT FOR SUBSEQUENT ANALYSIS OF METAL COMPONENTS IN VOLATILE ALKALI SOLUTION AND NON-VOLATILE ANION IN VOLATINE ACID SOLUTION AND METHOD AND APPARATUS FOR THE SUBSEQUENT ANALYSIS

[75] Inventor: Ushio Hase, Tokyo, Japan

[73] Assignee: NEC Corporation, Tokyo, Japan

[21] Appl. No.: 08/912,398

[22] Filed: Aug. 18, 1997

[30] Foreign Application Priority Data

Aug. 16, 1996 [JP] Japan .................................. 8-216401

[51] Int. Cl.$^7$ .............................. G01N 1/28; G01N 1/34
[52] U.S. Cl. .......................... 436/178; 204/522; 204/529; 204/532; 436/73; 436/150; 436/161
[58] Field of Search ................... 436/73, 79–84, 436/161, 163, 176, 177, 178, 150; 204/518, 520, 522, 529, 532

[56] References Cited

U.S. PATENT DOCUMENTS

| | | |
|---|---|---|
| 4,459,357 | 7/1984 | Jansen et al. . |
| 4,969,983 | 11/1990 | Parsi . |
| 4,999,098 | 3/1991 | Pohl et al. . |
| 5,518,622 | 5/1996 | Stillian et al. . |

FOREIGN PATENT DOCUMENTS 4-172244  6/1992  Japan .

*Primary Examiner*—Jan Ludlow
*Attorney, Agent, or Firm*—Young & Thompson

[57] ABSTRACT

Method of pre-treating a sample for metal analysis, the sample including a volatile alkali, by permeating the volatile alkali through a gas permeable membrane, dissolving the volatile alkali in an absorbent, passing ions through a first cation exchange membrane in electrical contact with an anode, reacting the volatile alkali with the ions, and passing the reacted volatile alkali through a second cation exchange membrane in electrical contact with a cathode, whereby the volatile alkali is removed from the sample.

7 Claims, 11 Drawing Sheets

METHOD AND APPARATUS FOR PRE-ANALYZING TREATMENT FOR SUBSEQUENT ANALYSIS OF METAL COMPONENTS IN VOLATILE ALKALI SOLUTION AND NON-VOLATILE ANION IN VOLATINE ACID SOLUTION AND METHOD AND APPARATUS FOR THE SUBSEQUENT ANALYSIS

BACKGROUND OF THE INVENTION

The present invention relates to a method and an apparatus for pre-analyzing treatment for subsequent analysis of metal components in volatile alkali solution and non-volatile anion in volatile acid solution and a method and an apparatus for the subsequent analysis thereof.

The following method has been known for improvement in detection sensitivity of ion-chromatography. An adsorbent is sorted concentration column for capturing analyzing components to be analyzed. A large amount of a sample solution is introduced into the concentration column for concentrating the analyzing components before an eluent is then introduced into the concentration column so that the concentrated component is separated at a separation column positioned in a downstream of the concentration column whereby the components are detected by a detector positioned in the downstream of the separation column.

In order to prevent the component peak from being spread, the adsorbent having not so high adsorbing capability is generally used to allow quick desorption of the captured components when the eluent is introduced into the concentration column. For that reason, if a sampling with no eluting ability such as ultrapure water is used, then the above column concentration method is effective and useful. If, however, a sampling with a high eluting ability such as chemicals is used, the above column concentration method is ineffective and not useful.

It is possible to suppress the eluting ability of the chemicals by diluting the chemicals with ultrapure water. Notwithstanding, if a highly pure chemical usefull for semiconductor manufacturing is analyzed, it is hard to make measurement thereof due to difficulty to obtain information about difference from blank test. It is therefore required to remove the main component of the sample solution prior to the introduction into the concentration column.

If the volatile components are the main components, a heat treatment is generally made as a pre-analyzing treatment for removal of the volatile components. Since, however, the heat treatment is a batch-treatment, it is difficult to realize the automation of the treatment. This method is time consuming.

The pre-analyzing treatment column may be used for treatment to selectively adsorb the main components of the sample solution This pre-analyzing treatment column may be applicable to the batch-treatment and the continuous treatments, it is however, required to regenerate or exchange the pre-analyzing treatment column.

Figure 1:
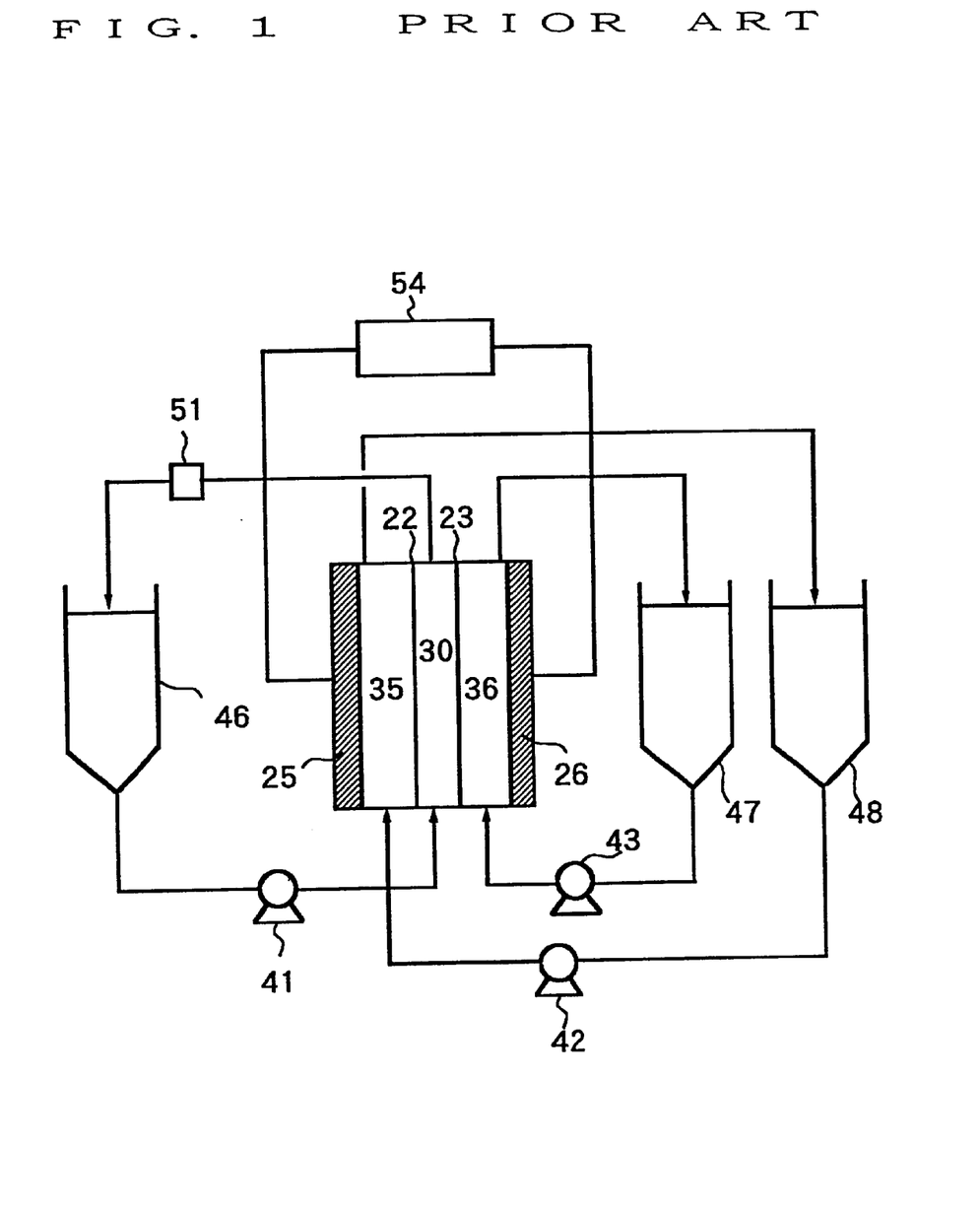
FIG. 1 is a block diagram illustrative of the conventional pre-analyzing treatment apparatus.

In the Japanese laid-open patent publication No. 4-172244, in order to settle the above problems, neutralization of the alkali components is made by use of an electro-dialysis for analysis of anion in the alkali solution. This conventional electrodialyzer is as illustrated in FIG. 1. An electrodialysis bath comprises an anode chamber 35, a cathode chamber 36, a sampling chamber 30 sandwiched by two cation exchange membranes 22 and 23, an anode 25 and a cathode 26. The anode 25 and the cathode 26 are connected in series to a dc power supply 54.

A sample solution is stored in a sample solution tank 46 and fed by a feeding pump 41 through a feeding line to the sampling chamber. 30 The sample solution used in the sampling chamber 30 is then returned to the sample solution tank 46. An anode solution is reserved in an anode solution tank 48 and fed by a feeding pump 42 into the anode chamber 35. A cathode solution is reserved in a cathode solution tank 47 and fed by a feeding pump 43 into the cathode chamber 36.

Hydrogen ions generated in the anode chamber 35 permeate through the cation exchange membrane 22 and then move into the sampling chamber 30. The cations already in the sampling chamber 30 then permeate through the cation exchange membrane 23 and then move into the cathode chamber 36. As a result, hydroxide ions in the sample solution are neutralized with hydrogen ions supplied from the anode chamber 35 for realizing the neutralization of the alkali solution. A neutralization monitor 51 is provided for monitoring the neutralization of the alkali solution. The neutralization monitor 51 may comprise a conductivity meter.

In case of the above conventional method using the electro-dialysis, not only the neutralization but also the demineralization may concurrently be carried out and the post-treatment solution can readily be used to the above column concentration method differently from the case of direct addition of the alkaline solution for neutralization In the Japanese laid-open patent publications Nos. 3-144356 and 7-134120, there is disclosed analysis of metal components in the acid solution.

By the way, for cleaning the silicon wafer in the semiconductor manufacturing processes, ammonia solution is one of the important chemicals. Ammonia solution is used to remove fine particles adhered from the silicon wafer surface. Metal ions in ammonia solution are likely to be adhered on the wafer surface in the cleaning process to provide undesirable influence to reliability and yield of the semiconductor devices. It is desired to maintain the metal ion concentration in ammonia solution. The ion-chromatograph is applicable to the in-line monitor for ultrapure water. It is, however, required to make automatic continuous pre-analyzing treatments for carrying out the in-line monitor for the metal impurities in ammonia solution.

The foregoing analyzing method and apparatus are applicable but only to ionic components having the opposite charge to the ions having been removed by the pre-analyzing treatment, for which reason in case of ammonia solution the anion components may be analyzed by the conventional technique but metal components could -never analyzed.

In the above circumstances, it had been required to develop novel method and apparatus for automatic and continuous pre-analyzing treatments for subsequent analysis of metal components in volatile alkali solution such as metal components in ammonia solution and non-volatile anion in volatile acid solution such as hydrochloric acid solution as well as a method and an apparatus for the above subsequent analysis.

SUMMARY OF THE INVENTION

Accordingly, it is an object of the present invention to provide a novel method for automatic and continuous pre-analyzing treatments for subsequent analysis of metal components in volatile alkali solution such as metal components in ammonia solution and non-volatile anion in volatile acid solution such as hydrochloric acid solution.

It is a further object of the present invention to provide a novel apparatus for automatic and continuous pre-analyzing treatments for subsequent analysis of metal components in volatile alkali solution such as metal components in ammonia solution and non-volatile anion in volatile acid solution such as hydrochloric acid solution.

It is a still further object of the present invention to provide a novel method for analysis of metal components in volatile alkali solution such as metal components in ammonia solution and non-volatile anion in volatile acid solution such as hydrochloric acid solution.

In accordance with the present invention, a gas-permeable membrane is used for separation of metal ions from a volatile component such as ammonia in the sample solution.

The above and other objects, features and advantages of the present invention will be apparent from the following descriptions.

BRIEF DESCRIPTIONS OF THE DRAWINGS

Preferred embodiments according to the present invention will be described with reference to the accompanying drawings.

DESCRIPTION OF THE PREFERRED EMBODIMENTS

The present invention provides a method of pre-analyzing treatment for analysis of metal ions in a sample solution including volatile alkali such as ammonia, wherein a volatile alkali component is allowed to permeate through a gas-permeable membrane for dissolving the volatile alkali component into an absorbent which is isolated by the gas-permeable membrane so that an volatile alkali component having been dissolved in the absorbent is reacted with ions in an electrolytic solution having permeated through a first cation exchange membrane positioned in an anode side before the volatile alkali component reacted with said ions is then allowed to permeate through a second cation exchange membrane positioned in a cathode side to attract the volatile alkali component to the cathode side so that the volatile alkali component is dissolved in an electrolytic solution in the cathode side for subsequent discharge of the electrolytic solution into which the volatile alkali component remains dissolved.

It is preferable that the absorbent comprises a non-volatile acid solution In this case, it is also preferable that the non-volatile acid solution comprises a sulfuric acid solution.

It is more preferable that the absorbent comprises ultra-pure water. In this case, it is not necessary to prepare a chemical reagent. The maintenance of the apparatus is relatively easy.

It is also preferable that the electrolytic solution comprises a non-volatile acid solution. In this case, it is also preferable that the non-volatile acid solution comprises a sulfuric acid solution.

It is more preferable that the electrolytic solution comprises ultrapure water. In this case, it is not necessary to prepare a chemical reagent. The maintenance of the apparatus is relatively easy.

The present invention also provides a method of pre-analyzing treatment for analysis of non-volatile cation such as sulfuric acid ions in a sample solution including volatile acid such as hydrochloric acid, wherein a volatile acid component is allowed to permeate through a gas-permeable membrane for dissolving the volatile acid component into an absorbent which is isolated by the gas-permeable membrane so that a volatile acid component having been dissolved in the absorbent is reacted with ions in an electrolytic solution having permeated through a first anion exchange membrane positioned in a cathode side before the volatile acid component reacted with said ions is then allowed to permeate through a second anion exchange membrane positioned in an anode side to attract the volatile acid component to the anode side so that the volatile acid component is dissolved in an electrolytic solution in the anode side for subsequent discharge of the electrolytic solution into which the volatile acid component remains dissolved.

It is preferable that the absorbent comprises a metal hydroxyoxide solution.

It is also preferable that the absorbent comprises a quaternary amine hydroxyoxide solution.

It is more preferable that the absorbent comprises ultra-pure water. In this case, it is not necessary to prepare a chemical reagent. The maintenance of the apparatus is relatively easy.

It is also preferable that the electrolytic solution comprises a metal hydroxyoxide solution.

It is also preferable that the electrolytic solution comprises a quaternary amine hydroxyoxide solution.

It is more preferable that the electrolytic solution comprises ultrapure water. In this case, it is not necessary to prepare a chemical reagent. The maintenance of the apparatus is relatively easy.

The present invention also provides an apparatus for a pre-analyzing treatment for analysis of metal ions in a sample solution including volatile alkali such as ammonia, wherein the apparatus has a module which comprises a sampling chamber isolated by gas-permeable membranes through which the sample solution is allowed to flow so that the sample solution can pass through said sampling chamber, first and second cation exchange membranes provided at opposite sides of the sampling chamber so that the first and second cation exchange membranes are separated by the sampling chamber, neutralization chambers provided between the gas-permeable membranes and the first and second cation exchange membranes, an anode chamber having an anode and being isolated from the first cation exchange membrane, a cathode chamber having a cathode and being isolated from the second cation exchange membrane, inlets and outlets for allowing an electrolytic solution to flow into and from the anode chamber and the cathode chamber as well as for allowing an absorption solution into and from the neutralization chamber. The apparatus also has a dc power supply applied across the anode and cathode as well as a feeding system for feeding the absorption solution into or from the neutralization chamber and feeding the sample solution into or from the sampling chamber as well as the electrolytic solution into or from the anode and cathode chambers.

It is possible to further provide a vibrator on the module for applying a continuous or discontinues vibration to the module for preventing that hydrogen or oxygen gases having been generated by the electrodialysis are adhered onto the first and second cation exchange membranes.

The present invention also provides an apparatus for a pre-analyzing treatment for analysis of sulfuric acid ions in a sample solution including volatile acid such as hydrochloric acid, wherein the apparatus has a module which comprises a sampling chamber isolated by gas-permeable membranes through which the sample solution is allowed to flow so that the sample solution can pass through said sampling chamber, first and second anion exchange membranes provided at opposite sides of the sampling chamber so that the first and second anion exchange membranes are separated by the sampling chamber, neutralization chambers provided between the gas-permeable membranes and the first and second anion exchange membranes, an anode chamber having an anode and being isolated from the first anion exchange membrane, a cathode chamber having a cathode and being isolated from the second anion exchange membrane, inlets and outlets for allowing an electrolytic solution to flow into and from the anode chamber and the cathode chamber as well as for allowing an absorption solution into and from the neutralization chamber. The apparatus also has a dc power supply applied across the anode and cathode as well as a feeding system for feeding the absorption solution into or from the neutralization chamber and feeding the sample solution into or from the sampling chamber as well as the electrolytic solution into or from the anode and cathode chambers.

It is possible to further provide a vibrator on the module for applying a continuous or discontinuos vibration to the module for preventing that hydrogen or oxygen gases having been generated by the electrodialysis are adhered onto the first and second anion exchange membranes.

The present invention also provides a method for analysis of metal ions in a sample solution including volatile alkali such as ammonia, wherein a monitor is made to a volatile alkali component in a sample solution being flowing out from a sampling chamber in a pre-analyzing treatment apparatus so as to have the pre-analyzing treatment apparatus be continued to recycle and flow out the sample solution until a monitoring value obtained by the monitor becomes drop to a reference value in stationary state.

It is preferable that if the monitoring value obtained by the monitor becomes drop to the reference value in stationary state, then an analyzing component in the sample solution from the pre-analyzing apparatus is concentrated and captured in a concentration column before an eluent is used for desorption of the concentrated and captured analyzing component for introduction of the eluent containing analyzing component into an analyzer which analyzes the analyzing component.

The present invention also provides a method for analysis of sulfuric acid ions in a sample solution including volatile acid such as hydrochloric acid, wherein a monitor is made to a volatile acid component in a sample solution being flowing out from a sampling chamber in a pre-analyzing treatment apparatus so as to have the pre-analyzing treatment apparatus be continued to recycle and flow out the sample solution until a monitoring value obtained by the monitor becomes drop to a reference value in stationary state.

It is preferable that if the monitoring value obtained by the monitor becomes drop to the reference value in stationary state, then an analyzing component in the sample solution from the pre-analyzing apparatus is concentrated and captured in a concentration column before an eluent is used for desorption of the concentrated and captured analyzing component for introduction of the eluent containing analyzing component into an analyzer which analyzes the analyzing component.

The present invention also provides an analyzer for analysis of metal ions in a sample solution including volatile alkali component such as ammonia, wherein the analyzer comprises a pre-analyzing treatment apparatus, a feeding system for feeding the sample solution, a neutralization monitor for monitoring a volatile alkali component in the sample solution, a concentration column for concentrating and capturing an analyzing component in the sample solution having been treated by said pre-analyzing treatment apparatus, a separation column for providing an eluent to the analyzing component concentrated and captured by the concentration column for desorption of said analyzing component into said eluent, a flow passage switching valve for providing a circulation flow passage which allows the sample solution to flow into or flow out of the pre-analyzing treatment apparatus without passing through the concentration column until a monitoring value obtained by the neutralization monitor becomes drop to a reference value in stationary state, and after the monitoring value has remained below the reference value, the flow passage switching valve providing a non-circulation flow passage which introduces the eluent into said concentration column so that the analyzing component is made adsorption from the sample solution and introduced along with the eluent into the separation column, and a detector for receiving an introduction of the eluent with the analyzing component from the separation column to detect the analyzing component.

It is preferable that the analyzer comprises a pre-analyzing treatment apparatus, a feeding system for feeding the sample solution, a neutralization monitor for monitoring a volatile alkali component in the sample solution, a concentration column for concentrating and capturing an analyzing component in the sample solution having been treated by said pre-analyzing treatment apparatus, a separation column for providing an eluent to the analyzing component concentrated and captured by the concentration column for desorption of said analyzing component into said eluent, a first feeding system for feeding the sample solution, a second feeding system for feeding the solution to the pre-analyzing treatment apparatus, a measuring tube having a predetermined capacity, a flow passage allowing the solution treated by the pre-analyzing treatment apparatus to be introduced into the concentration column, a first flow passage switching valve for providing a circulation flow passage which allows the sample solution to flow into or flow out of the pre-analyzing treatment apparatus without passing through the concentration column until the monitoring value obtained by the neutralization monitor becomes drop to the reference value in stationary state, and after the monitoring value has remained below the reference value, the first flow passage switching valve providing a non-circulation flow passage which introduces the eluent into said concentration column so that the analyzing component is made adsorption from the sample solution and introduced along with the eluent into the separation column, a second flow passage switching valve switching a flow passage between connection to the pre-analyzing treatment apparatus and connection to the measuring tube for allowing the sample solution to be fed into the measuring tube by the first feeding system for reserving the same, a third flow passage switching valve switching a flow passage between a flow passage for introduction of a diluting water by the second feeding system into the second flow passage switching valve and a circulation flow passage connecting among the second feeding system, the second flow passage switching valve connecting to the pre-analyzing treatment apparatus, the first flow passage switching valve and the pre-analyzing treatment apparatus, and a detector for receiving an introduction of the eluent with the analyzing component from the separation column to detect the analyzing component It is preferable that the neutralization monitor comprises a conductivity meter.

It is preferable that the neutralization monitor comprises a pH meter.

The present invention also provides an analyzer for analysis of sulfuric acid ions in a sample solution including volatile acid component such as hydrochloric acid, wherein the analyzer comprises a pre-analyzing treatment apparatus, a feeding system for feeding the sample solution, a neutralization monitor for monitoring a volatile acid component in the sample solution, a concentration column for concentrating and capturing an analyzing component in the sample solution having been treated by said pre-analyzing treatment apparatus, a separation column for providing an eluent to the analyzing component concentrated and captured by the concentration column for desorption of said analyzing component into said eluent, a flow passage switching valve for providing a circulation flow passage which allows the sample solution to flow into or flow out of the pre-analyzing treatment apparatus without passing through the concentration column until a monitoring value obtained by the neutralization monitor becomes drop to a reference value in stationary state, and after the monitoring value has remained below the reference value, the flow passage switching valve providing a non-circulation flow passage which introduces the eluent into said concentration column so that the analyzing component is made adsorption from the sample solution and introduced along with the eluent into the separation column, and a detector for receiving an introduction of tile eluent with the analyzing component from the separation column to detect the analyzing component.

It is preferable that the analyzer comprises a pre-analyzing treatment apparatus, a feeding system for feeding the sample solution, a neutralization monitor for monitoring a volatile acid component in the sample solution, a concentration column for concentrating and capturing an analyzing component in the sample solution having been treated by said pre-analyzing treatment apparatus, a separation column for providing an eluent to the analyzing component concentrated and captured by the concentration column for desorption of said analyzing component into said eluent, a first feeding system for feeding the sample solution, a second feeding system for feeding the solution to the pre-analyzing treatment apparatus, a measuring tube having a predetermined capacity, a flow passage allowing the solution treated by the pre-analyzing treatment apparatus to be introduced into the concentration column, a first flow passage switching valve for providing a circulation flow passage which allows the sample solution to flow into or flow out of the pre-analyzing treatment apparatus without passing through the concentration column until the monitoring value obtained by the neutralization monitor becomes drop to the reference value in stationary state, and after the monitoring value has remained below the reference value, the first flow passage switching valve providing a non-circulation flow passage which introduces the eluent into said concentration column so that the analyzing component is made adsorption from the sample solution and introduced along with the eluent into the separation column, a second flow passage switching valve switching a flow passage between connection to the pre-analyzing treatment apparatus and connection to the measuring tube for allowing the sample solution to be fed into the measuring tube by the first feeding system for reserving the same, a third flow passage switching valve switching a flow passage between a flow passage for introduction of a diluting water by the second feeding system into the second flow passage switching valve and a circulation flow passage connecting among the second feeding system, the second flow passage switching valve connecting to the pre-analyzing treatment apparatus, the first flow passage switching valve and the pre-analyzing treatment apparatus, and a detector for receiving an introduction of the eluent with the analyzing component from the separation column to detect the analyzing component.

It is preferable that the neutralization monitor comprises a conductivity meter.

It is also preferable that the neutralization monitor comprises a pH meter.

The present invention also provides a method for analysis of metal ions in a sample solution including volatile alkali such as ammonia, wherein a diluting water by is introduced by a third flow passage switching valve into a flow passage and then a sample solution is reserved by a second flow passage switching valve into a measuring tube, and thereafter the first flow passage switching valve provides a circulation flow passage which allows the sample solution to flow into or flow out of the pre-analyzing treatment apparatus without passing through the concentration column until the monitoring value obtained by the neutralization monitor becomes drop to the reference value in stationary state, and after the monitoring value has remained below the reference value, the first flow passage switching valve provides a non-circulation flow passage which introduces the eluent into said concentration column so that the analyzing component is made adsorption from the sample solution and introduced along with the eluent into the separation column, so that the eluent is introduced with the analyzing component from the separation column into a detector for detecting the analyzing component. This method is suitable to a high concentration volatile alkali component is included in the sample solution.

It is possible not to use the neutralization monitor wherein the first flow passage switching valve provides a circulation flow passage which allows the sample solution to flow into or flow out of the pre-analyzing treatment apparatus without passing through the concentration column for a predetermined time period, and thereafter the first flow passage switching valve provides a non-circulation flow passage which introduces the eluent into said concentration column so that the analyzing component is made adsorption from the sample solution and introduced along with the eluent into the separation column.

The present invention also provides a method for analysis of sulfuric acid ions in a sample solution including volatile acid such as hydrochloric acid, wherein a diluting water by is introduced by a third flow passage switching valve into a flow passage and then an sample solution is reserved by a second flow passage switching valve into a measuring tube, and thereafter the first flow passage switching valve provides a circulation flow passage which allows the sample solution to flow into or flow out of the pre-analyzing treatment apparatus without passing through the concentration column until the monitoring value obtained by the neutralization monitor becomes drop to the reference value in stationary state, and after the monitoring value has remained below the reference value, the first flow passage switching valve provides a non-circulation flow passage which introduces the diluting water into said concentration column so that the analyzing component is made adsorption from the sample solution and introduced along with the eluent into the separation chamber, so that the eluent is introduced with the analyzing component from the separation column into a detector for detecting the analyzing component. This method is suitable to a high concentration volatile acid component is included in the sample solution.

It is possible not to use the neutralization monitor wherein the first flow passage switching valve provides a circulation flow passage which allows the sample solution to flow into or flow out of the pre-analyzing treatment apparatus without passing through the concentration column for a predetermined time period, and thereafter the first flow passage switching valve provides a non-circulation flow passage which introduces the diluting water into said concentration column so that the analyzing component is made adsorption from the sample solution and introduced along with the eluent into the separation column.

Figure 2:
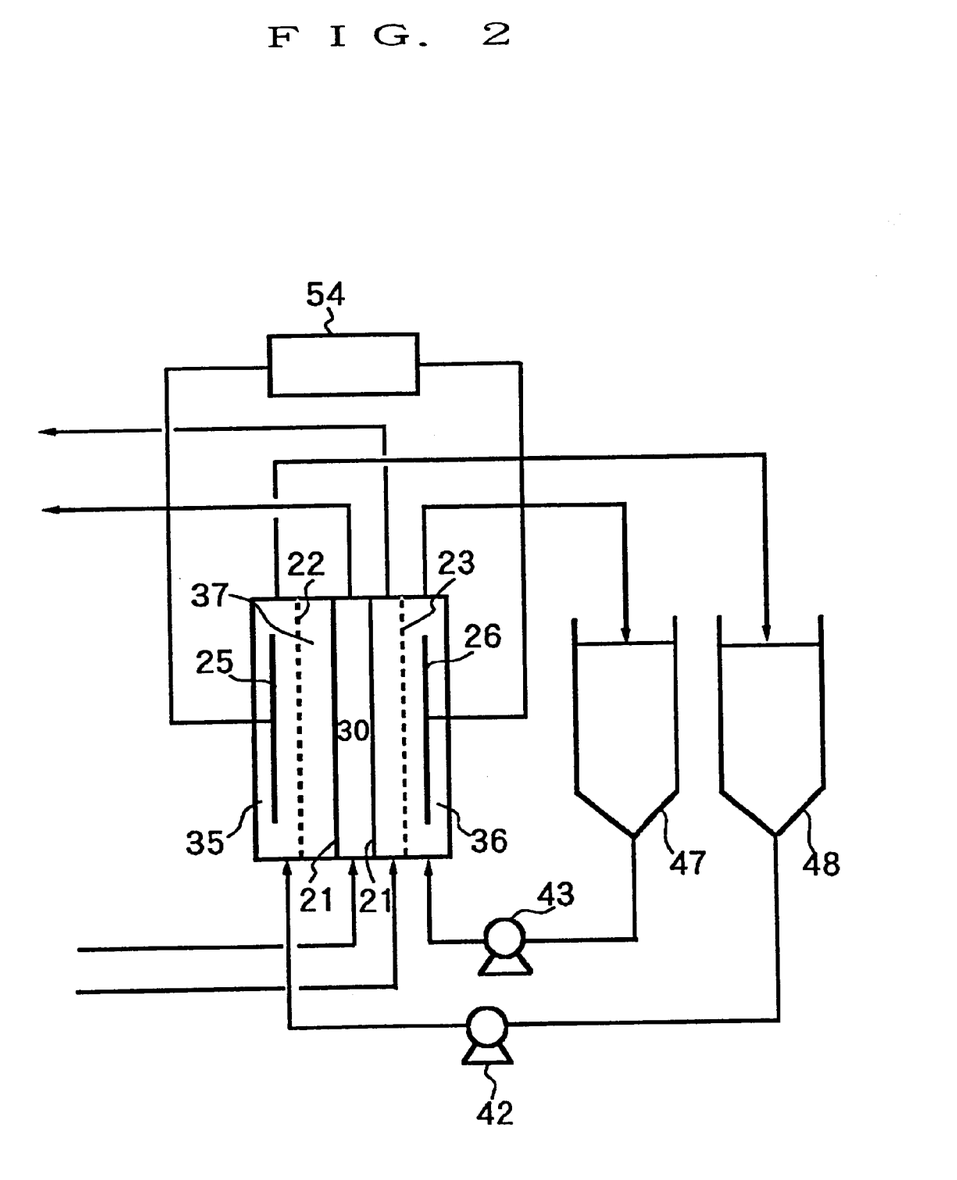
FIG. 2 is a block diagram illustrative of a novel pre-analyzing treatment apparatus in a first embodiment according to the present invention.
Figure 3:
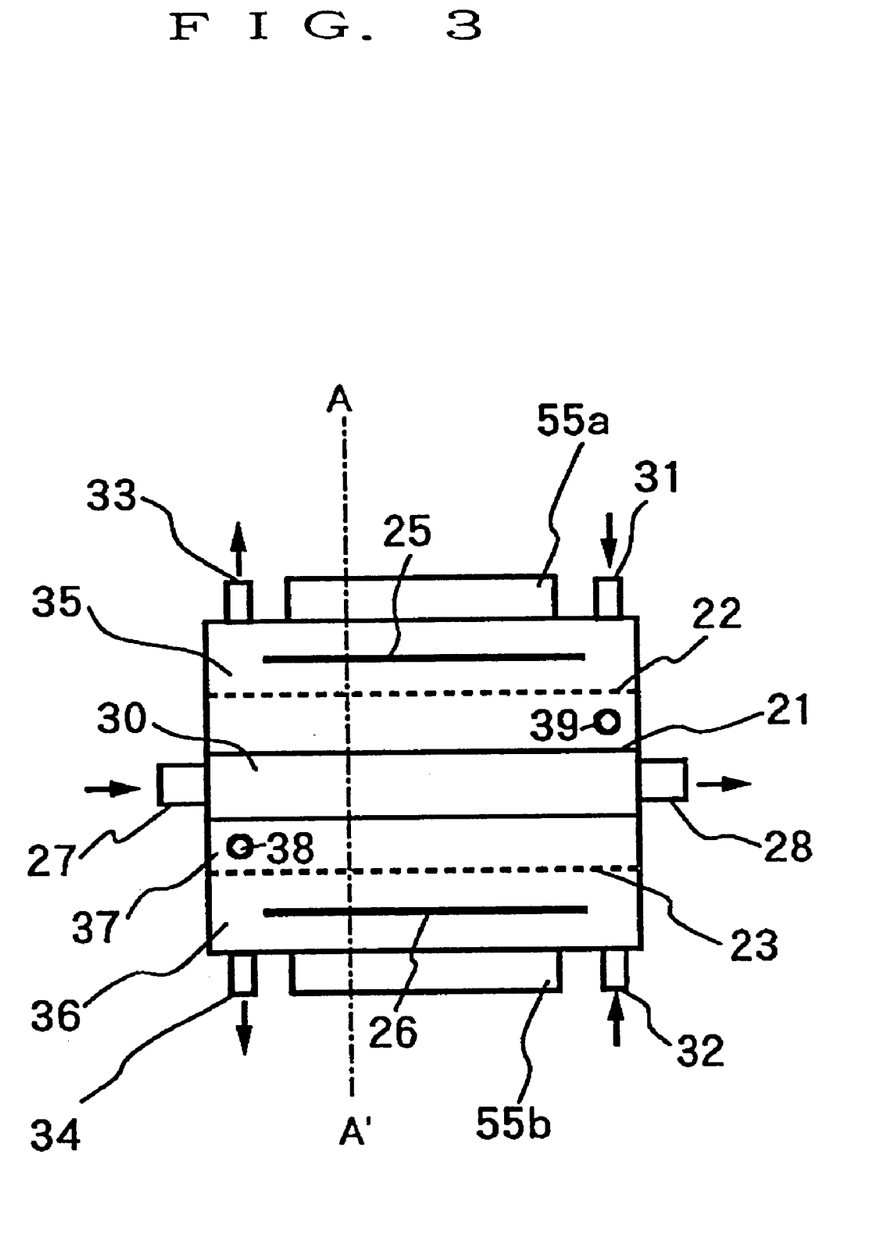
FIG. 3 is a block diagram illustrative of a module of a novel pre-analyzing treatment apparatus of FIG. 2 in a first embodiment according to the present invention.
Figure 4:
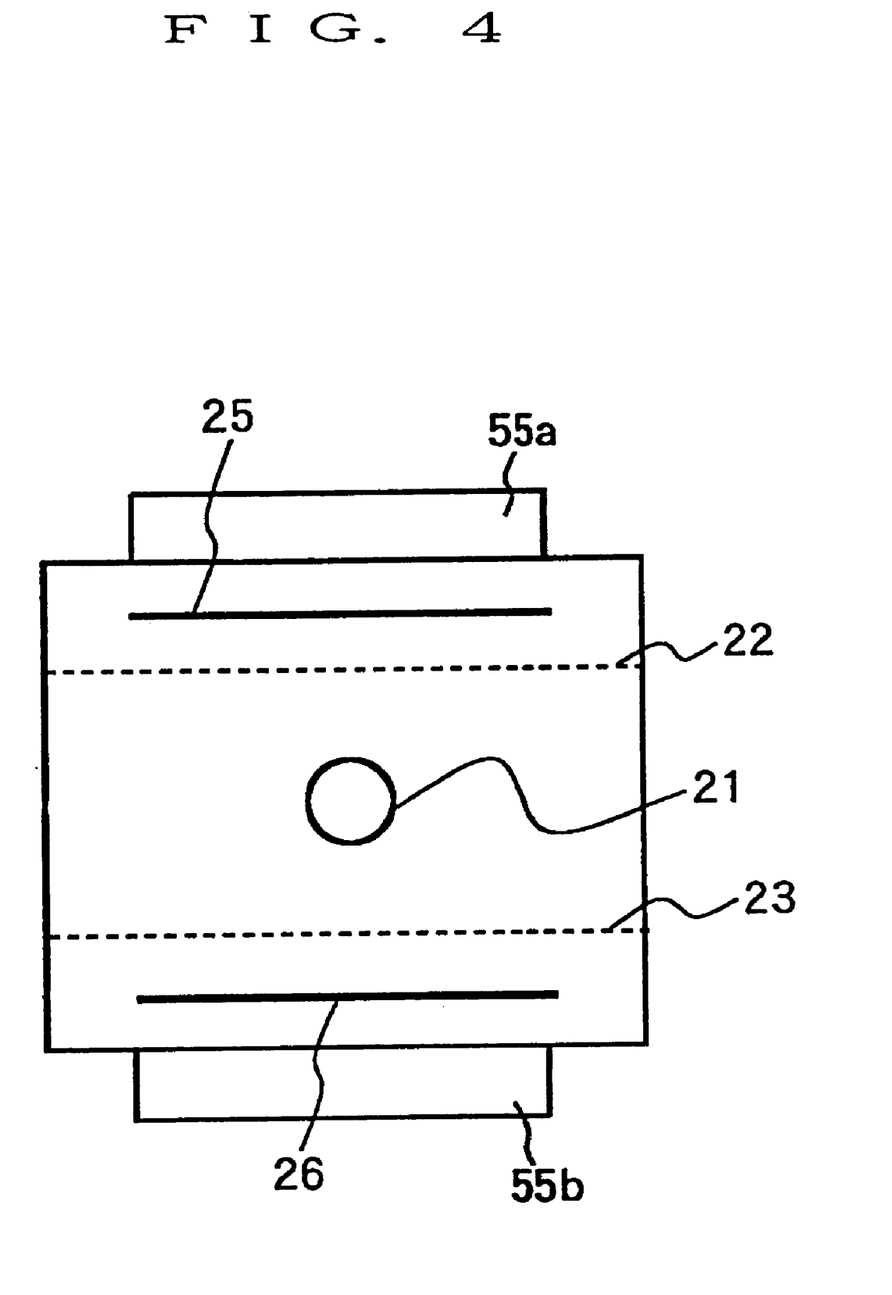
FIG. 4 is a cross sectional elevation view taken along an A—A' line in FIG. 3 illustrative of a module of a novel pre-analyzing treatment apparatus of FIG. 2 in a first embodiment according to the present invention.

A first embodiment according to the present invention will be described with reference to FIG. 2 which is a block diagram illustrative of a novel pre-analyzing treatment apparatus in a first embodiment according to the present invention. FIG. 3 is a block diagram illustrative of a module of a novel pre-analyzing treatment apparatus of FIG. 2 in a first embodiment according to the present invention. FIG. 4 is a cross sectional elevation view taken along an A—A' line in FIG. 3 illustrative of a module of a novel pre-analyzing treatment apparatus of FIG. 2 in a first embodiment according to the present invention.

The apparatus is provided for a pre-analyzing treatment for analysis of metal ions in a sample solution including volatile alkali such as ammonia. The apparatus has a module which comprises a sample chamber 30 isolated by gas-permeable membranes 21 through which the sample solution is allowed to permeate so that the sample solution can pass through said sample chamber, first and second cation exchange membranes 22 and 23 provided at opposite sides of the sample chamber 30 so that the first and second cation exchange membranes 22 and 23 are separated by the sample chamber 30, neutralization chambers 37 provided between the gas-permeable membranes 21 and the first and second cation exchange membranes 22 and 23, an anode chamber 35 having an anode 25 and being isolated from the first cation exchange membrane 22, a cathode chamber 36 having a cathode 26 and being isolated from the second cation exchange membrane 23, inlets 31 and 32 and outlets 33 and 34 for allowing an electrolytic solution to flow into and from the anode chamber 35 and the cathode chamber 36 as well as inlet 38 and outlet 39 for allowing an absorption solution into and from the neutralization chamber 37. The apparatus also has a dc power supply 54 applied across the anode and cathode as well as a feeding system for feeding the absorption solution into or from the neutralization chamber 37 and feeding the sample solution into or from the sample chamber 30 as well as the electrolytic solution into or from the anode and cathode chambers 35 and 36. Vibrators 55a and 55b are provided on the module for applying a continuous or discontinues vibration to the module for preventing that hydrogen or oxygen gases having been generated by the electrodialysis is adhered onto the first and second cation exchange membranes 22 and 23.

Figure 5:
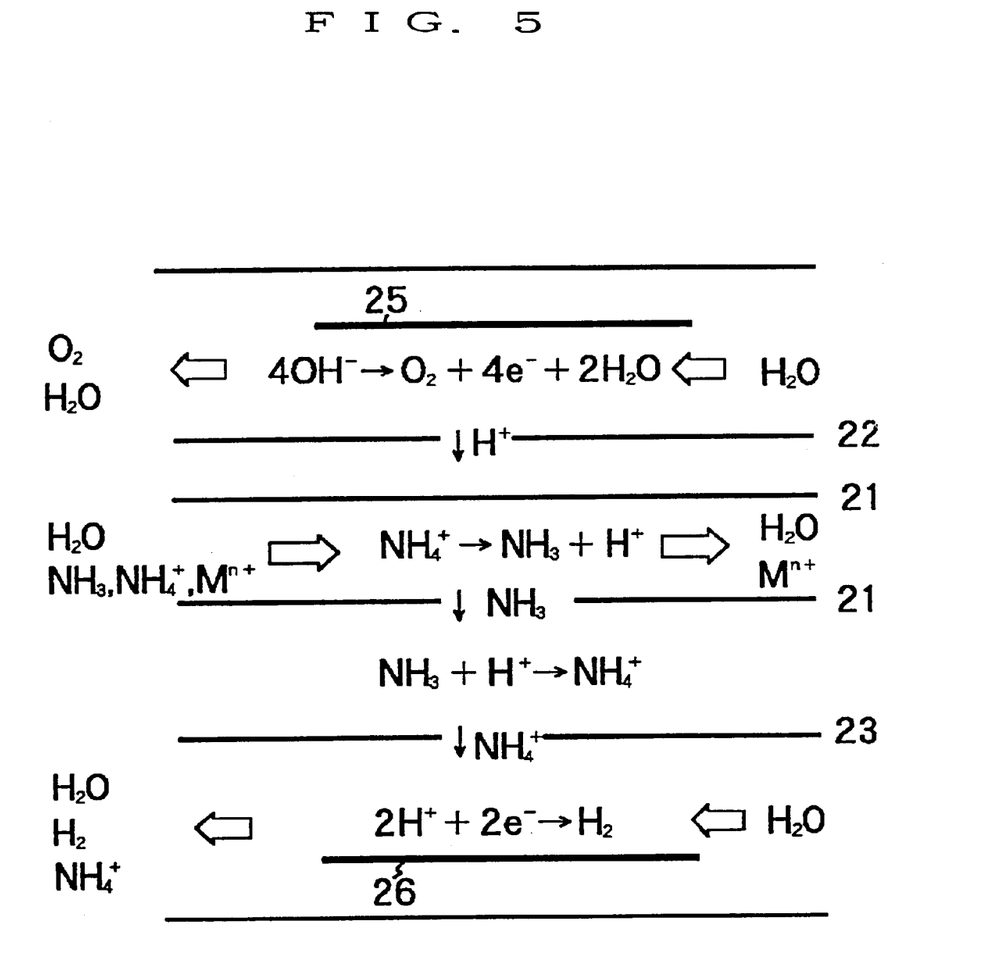
FIG. 5 is a view illustrative of chemical reactions appearing in a module of a novel pre-analyzing treatment apparatus of FIG. 2 in a first embodiment according to the present invention.

FIG. 5 is a view illustrative of chemical reactions appearing in a module of a novel pre-analyzing treatment apparatus of FIG. 2 in a first embodiment according to the present invention. The volatile acid component is allowed to permeate through the gas-permeable membranes 21 for dissolving the volatile acid component into the absorbent which is isolated by the gas-permeable membranes 21 so that the volatile alkali component having been dissolved in the absorbent is reacted with ions in an electrolytic solution having permeated through the first cation exchange membrane 22 positioned in an anode side before the volatile alkali component reacted with said ions is then allowed to permeate through the second cation exchange membrane 23 positioned in a cathode side to attract the volatile alkali component to the cathode side so that the volatile alkali component is dissolved in an electrolytic solution in the cathode side for subsequent discharge of the electrolytic solution into which the volatile alkali component remains dissolved.

Figure 10:
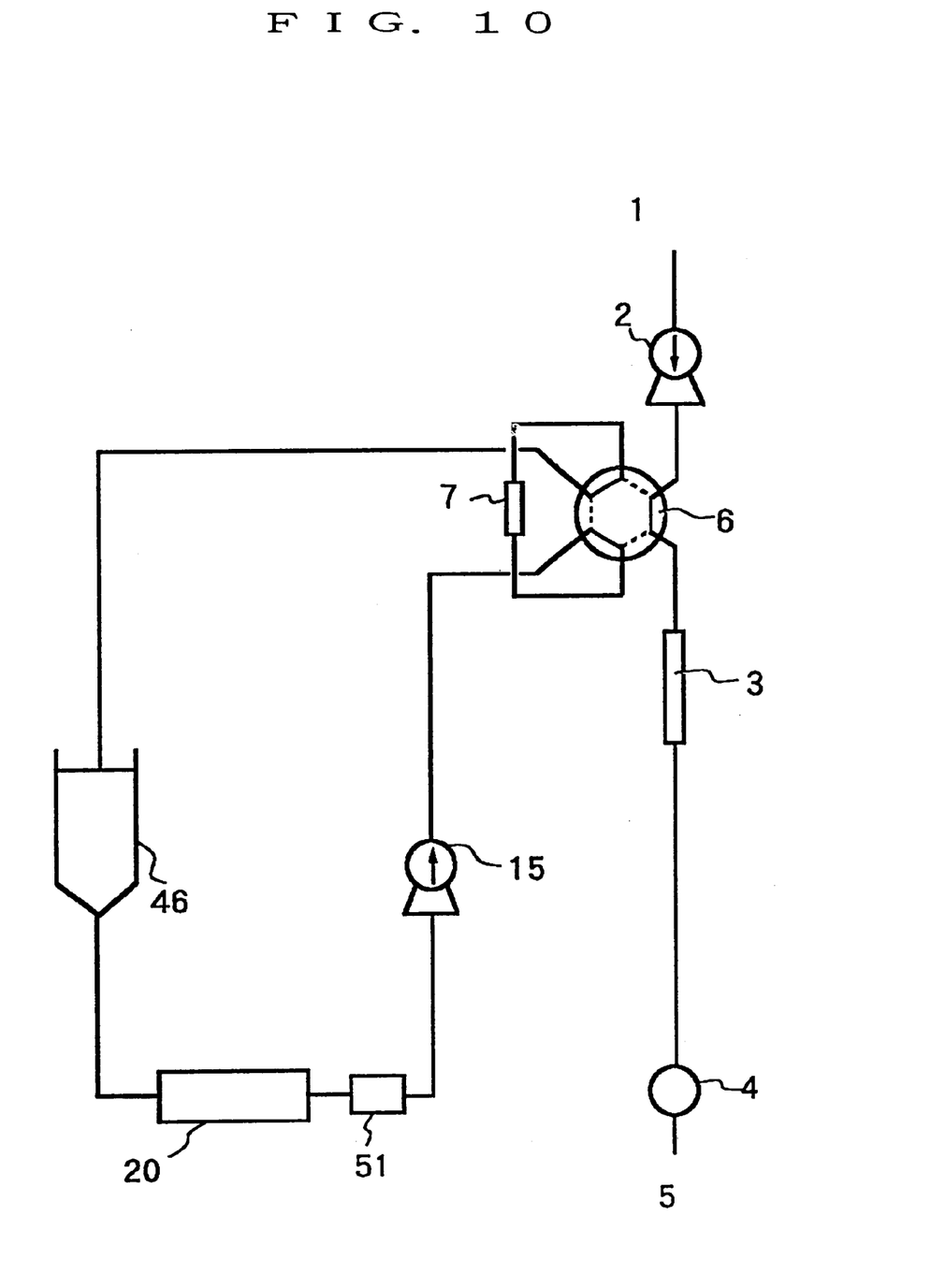
FIG. 10 is a block diagram illustrative of an analyzer used in first and second embodiments according to the present invention.

FIG. 10 is a block diagram illustrative of an analyzer used in first and second embodiments according to the present invention. The analyzer comprises a pre-analyzing treatment apparatus 20, a feeding system 15 for feeding the sample solution, a neutralization monitor 51 for monitoring a volatile alkali component in the sample solution, a concentration column 7 for concentrating and capturing an analyzing component in the sample solution having been treated by said pre-analyzing treatment apparatus 20, a separation column 3 for providing an eluent 1 to the analyzing component concentrated and captured by the concentration column for desorption of said analyzing component into said eluent, a flow passage switching valve 6 for providing a circulation flow passage which allows the sample solution to flow into or flow out of the pre-analyzing treatment apparatus without passing through the concentration column until a monitoring value obtained by the neutralization monitor 51 becomes drop to a reference value in stationary state, and after the monitoring value has remained below the reference value, the flow passage switching valve 6 providing a non-circulation flow passage which introduces the eluent into said concentration column 7 so that the analyzing component is made adsorption from the sample solution and introduced along with the eluent into the separation column 3, and a detector 4 for receiving an introduction of the eluent 1 with the analyzing component from the separation column to detect the analyzing component.

Figure 6:
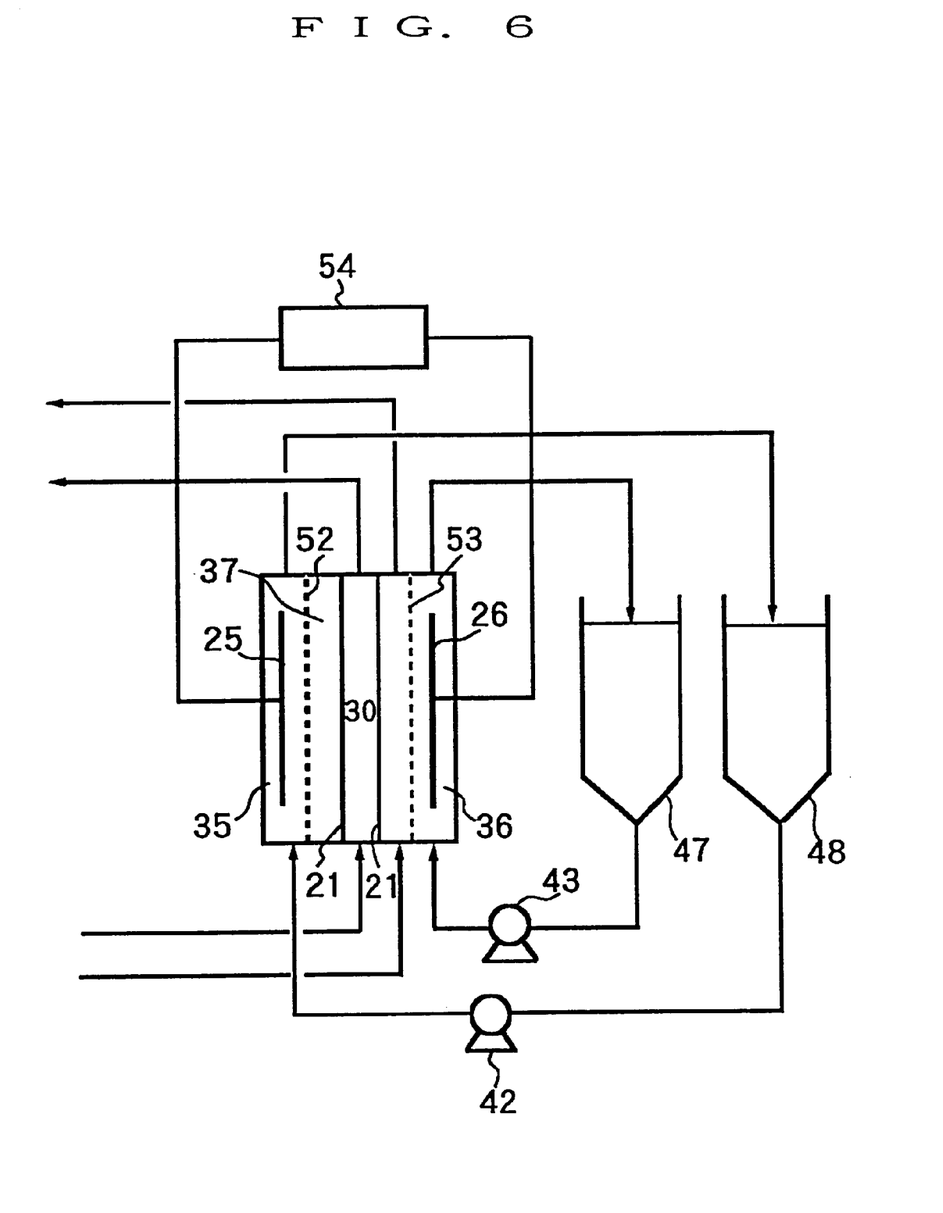
FIG. 6 is a block diagram illustrative of a novel pre-analyzing treatment apparatus in a second embodiment according to the present invention.
Figure 7:
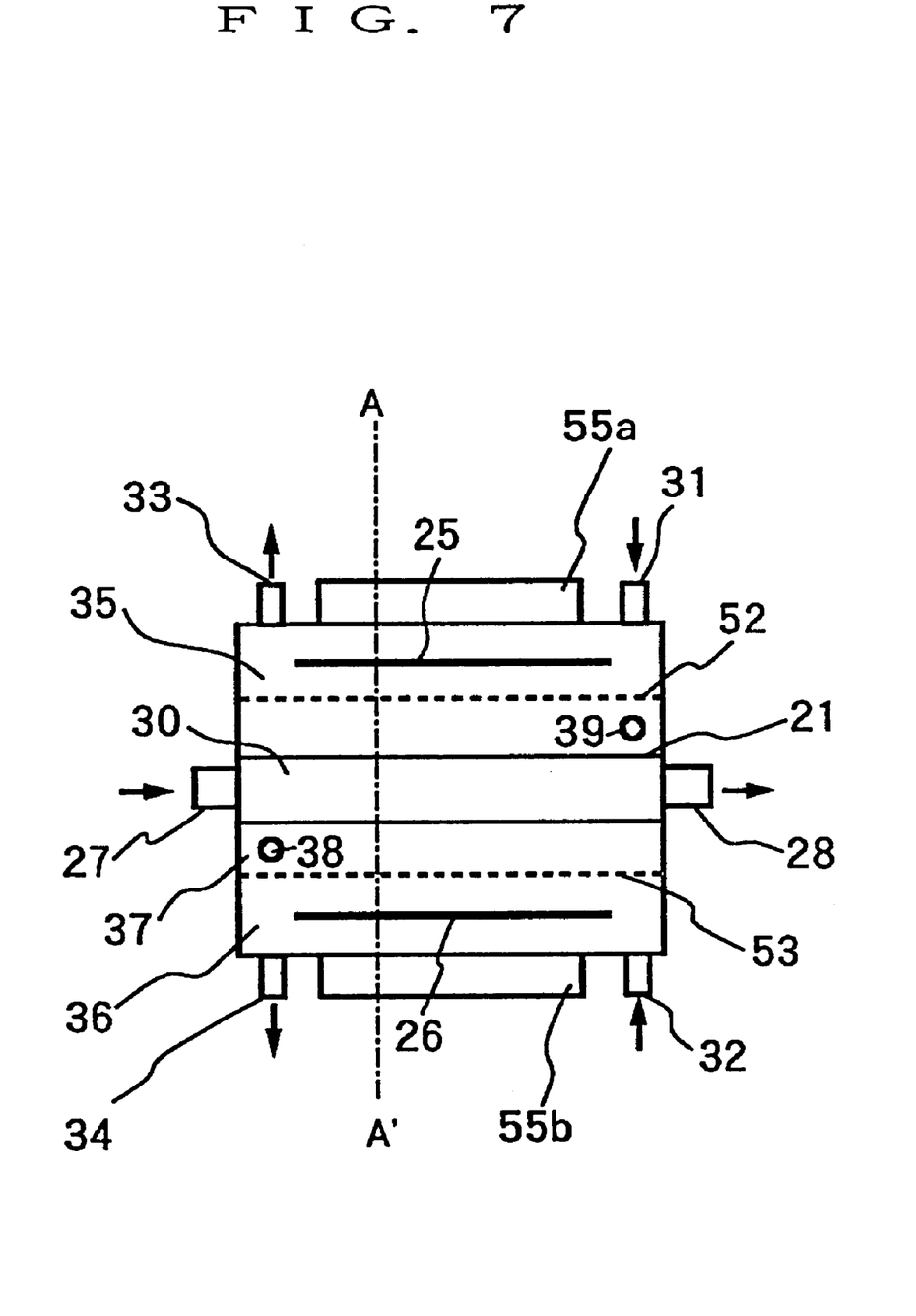
FIG. 7 is a block diagram illustrative of a module of a novel pre-analyzing treatment apparatus of FIG. 6 in a second embodiment according to the present invention.
Figure 8:
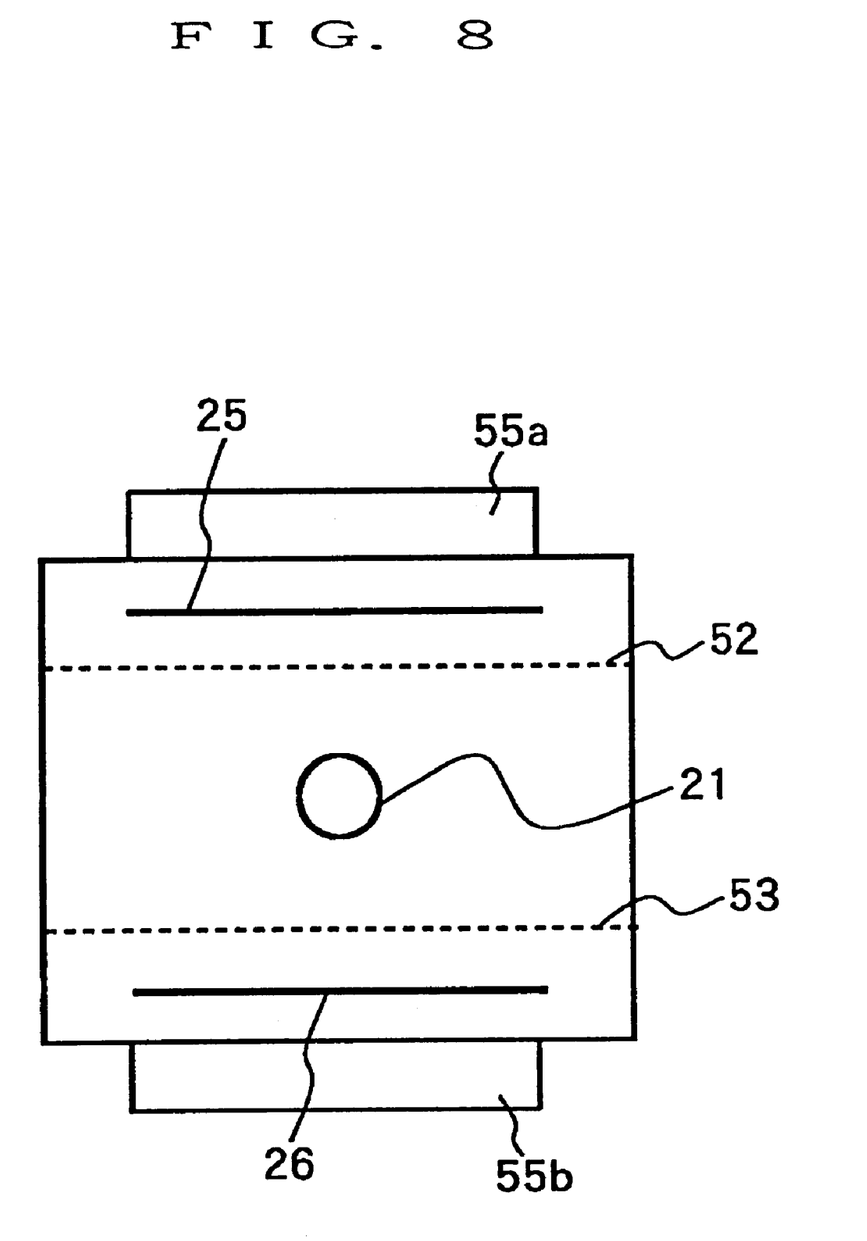
FIG. 8 is a cross sectional elevation view taken along an A—A' line in FIG. 7 illustrative of a module of a novel pre-analyzing treatment apparatus of FIG. 6 in a second embodiment according to the present invention.

A second embodiment according to the present invention will be described with reference to FIG. 6 which is a block diagram illustrative of a novel pre-analyzing treatment apparatus in a second embodiment according to the present invention. FIG. 7 is a block diagram illustrative of a module of a novel pre-analyzing treatment apparatus of FIG. 6 in a second embodiment according to the present invention. FIG. 8 is a cross sectional elevation view taken along an A—A' line in FIG. 2 illustrative of a module of a novel pre-analyzing treatment apparatus of PIG. 6 in a second embodiment according to the present invention.

An apparatus is provided for a pre-analyzing treatment for analysis of sulfuric acid ions in a sample solution including volatile acid such as hydrochloric acid. The apparatus has a module which comprises a sample chamber 30 isolated by gas-permeable membranes 21 through which the sample solution is allowed to permeate so that the sample solution can pass through said sample chamber 30, first and second anion exchange membranes 52 and 53 provided at opposite sides of the sample chamber so that the first and second anion exchange membranes are separated by the sample chamber, neutralization chambers 52 and 53 provided between the gas-permeable membranes 21 and the first and second anion exchange membranes 52 and 53, an anode chamber 35 having an anode 25 and being isolated from the first anion exchange membrane 52, a cathode chamber 36 having a cathode 26 and being isolated from the second anion exchange membrane 53, inlets 31, 32, 38 and outlets 33, 34, 39 for allowing an electrolytic solution to flow into and from the anode chamber 35 and the cathode chamber 36 as well as for allowing an absorption solution into and from the neutralization chamber. The apparatus also has a dc power supply applied across the anode and cathode as well as a feeding system for feeding the absorption solution into or from the neutralization chamber and feeding the sample solution into or from the sample chamber as well as the electrolytic solution into or from the anode and cathode chambers. Vibrators 55*a* and 55*b* are provided on the module for applying a continuous or discontinues vibration to the module for preventing that hydrogen or oxygen gases having been generated by the electrodialysis are adhered onto the first and second anion exchange membranes 52 and 53.

Figure 9:
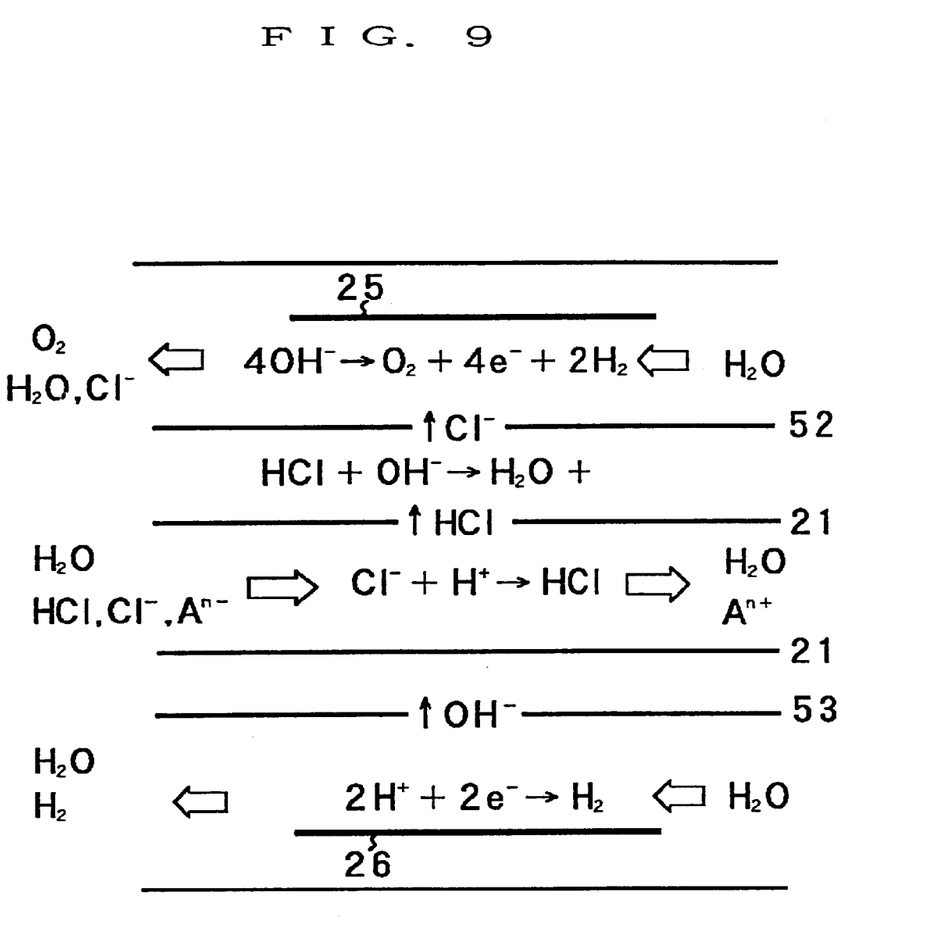
FIG. 9 is a view illustrative of chemical reactions appearing in a module of a novel pre-analyzing treatment apparatus of FIG. 6 in a second embodiment according to the present invention.

FIG. 9 is a view illustrative of chemical reactions appearing in a module of a novel pre-analyzing treatment apparatus of FIG. 6 in a second embodiment according to the present invention. The volatile acid component is allowed to permeate through the gas-permeable membrane for dissolving the volatile acid component into the absorbent which is isolated by the gas-permeable membrane so that an volatile acid component having been dissolved in the absorbent is reacted with ions in an electrolytic solution having permeated through a first anion exchange membrane positioned in a cathode side before the volatile acid component reacted with said ions is then allowed to permeate through a second anion exchange membrane positioned in an anode side to attract the volatile acid component to the anode side so that the volatile acid component is dissolved in an electrolytic solution in the anode side for subsequent discharge of the electrolytic solution into which the volatile acid component remains dissolved.

FIG. 10 is a block diagram illustrative of an analyzer used in first and second embodiments according to the present invention. The analyzer comprises a pre-analyzing treatment apparatus 20, a feeding system 15 for feeding the sample solution, a neutralization monitor 51 for monitoring a volatile alkali component in the sample solution, a concentration column 7 for concentrating and capturing an analyzing component in the sample solution having been treated by said pre-analyzing treatment apparatus 20, a separation column 3 for providing an eluent 1 to the analyzing component concentrated and captured by the concentration column for desorption of said analyzing component into said eluent, a flow passage switching valve 6 for providing a circulation flow passage which allows the sample solution to flow into or flow out of the pre-analyzing treatment apparatus without passing through the concentration column until a monitoring value obtained by the neutralization monitor 51 becomes drop to a reference value in stationary state, and after the monitoring value has remained below the reference value, the flow passage switching valve 6 providing a non-circulation flow passage which introduces the eluent into said concentration column 7 so that the analyzing component is made adsorption from the sample solution and introduced along with the eluent into the separation column 3, and a detector 4 for receiving an introduction of the eluent 1 with the analyzing component from the separation column to detect the analyzing component.

Figure 11:
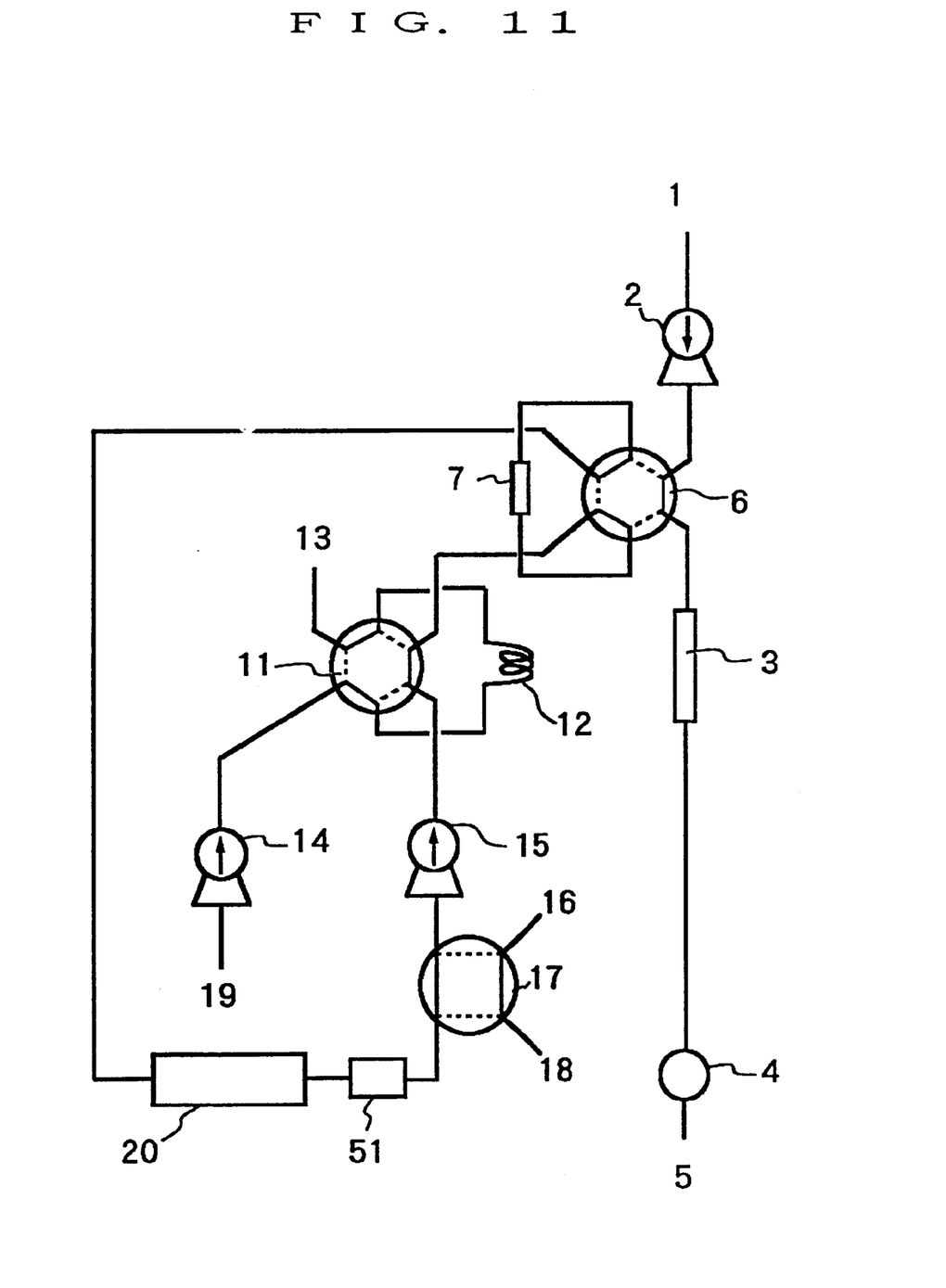
FIG. 11 is a block diagram illustrative of another analyzer used in a third embodiment according to the present invention

As a modification, the analyzer may comprises as illustrated in FIG. 11.

Whereas modifications of the present invention will be apparent to a person having ordinary skill in the art, to which the invention pertains, it is to be understood that embodiments as shown and described by way of illustrations are by no means intended to be considered in a limiting sense. Accordingly, it is to be intended to cover by claims all modifications which fall within the spirit and scope of the present invention.

What is claimed is:

1. A method of pre-treating a sample having metal ions in a volatile alkali, wherein the volatile alkali permeates through a gas-permeable membrane and is dissolved in an absorbent which is isolated from the volatile alkali by the gas-permeable membrane so that the volatile alkali, having been dissolved in the absorbent, is reacted with ions in a first electrolytic solution to form a reaction product, said ions having permeated through a first cation exchange membrane that is in electrical contact with an anode before the volatile alkali is reacted with said ions, and the reaction product then permeates through a second cation exchange membrane positioned in electrical contact with a cathode so that the reaction product is dissolved in a second electrolytic solution for subsequent discharge of the second electrolytic solution in which the reaction product remains dissolved.

2. The method as claimed in claim 1, wherein the absorbent comprises a non-volatile acid solution.

3. The method as claimed in claim 1, wherein the absorbent comprises ultrapure water.

4. The method as claimed in claim 1, wherein the first electrolytic solution comprises a non-volatile acid solution.

5. The method as claimed in claim 4, wherein the non-volatile acid solution comprises a sulfuric acid solution.

6. The method as claimed in claim 1, wherein the first electrolytic solution comprises ultrapure water.

7. A method of pre-treating a sample for metal analysis, the sample including a volatile alkali, the method comprising the steps of:

permeating the volatile alkali through a gas permeable membrane;

dissolving the volatile alkali in an absorbent;

passing ions through a first cation exchange membrane in electrical contact with an anode;

reacting the volatile alkali with the ions; and passing the reacted volatile alkali through a second cation exchange membrane in electrical contact with a cathode, whereby the volatile alkali is removed from the sample.

* * * * *